United States Patent
Sawanoi et al.

(10) Patent No.: US 9,131,859 B2
(45) Date of Patent: Sep. 15, 2015

(54) BLOOD PRESSURE MEASUREMENT APPARATUS, RECORDING MEDIUM THAT RECORDS BLOOD PRESSURE DERIVATION PROGRAM, AND BLOOD PRESSURE DERIVATION METHOD

(75) Inventors: Yukiya Sawanoi, Kyoto (JP); Kenji Fujii, Kyoto (JP); Naomi Matsumura, Kyoto (JP); Reiji Fujita, Kyoto (JP); Kenichi Yamakoshi, Kanazawa (JP); Masamichi Nogawa, Kanazawa (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 529 days.

(21) Appl. No.: 12/922,462

(22) PCT Filed: Mar. 13, 2009

(86) PCT No.: PCT/JP2009/054856
§ 371 (c)(1),
(2), (4) Date: Sep. 14, 2010

(87) PCT Pub. No.: WO2009/113653
PCT Pub. Date: Sep. 17, 2009

(65) Prior Publication Data
US 2011/0021927 A1    Jan. 27, 2011

(30) Foreign Application Priority Data
Mar. 14, 2008    (JP) ................................. 2008-066523

(51) Int. Cl.
*A61B 5/02*      (2006.01)
*A61B 5/0225*    (2006.01)
(Continued)

(52) U.S. Cl.
CPC ............... *A61B 5/02255* (2013.01); *A61B 5/02* (2013.01); *A61B 5/7239* (2013.01); *A61B 5/0261* (2013.01)

(58) Field of Classification Search
CPC ..... A61B 5/02; A61B 5/02255; A61B 5/7239
USPC .................................. 600/301, 479, 480–507
See application file for complete search history.

(56) References Cited

U.S. PATENT DOCUMENTS 4,524,777 A    6/1985   Kisioka et al.
4,776,344 A * 10/1988   Shirasaki et al. ............. 600/494
(Continued)

FOREIGN PATENT DOCUMENTS

JP    62-170225 A    7/1987
JP    3-81375 A      4/1991
(Continued)

OTHER PUBLICATIONS

Russian Office Action for Russian Application No. 2010142015, mailed on Sep. 30, 2011, and English translation thereof (9 pages).
(Continued)

*Primary Examiner* — Jacqueline Cheng
*Assistant Examiner* — Puya Agahi
(74) *Attorney, Agent, or Firm* — Osha Liang LLP

(57) ABSTRACT

A blood pressure measurement apparatus includes a derivation control unit that performs derivation control to derive a blood pressure of a measured person. The derivation control unit includes an envelope extracting unit to extract an envelope of a volume pulse wave based on an arterial volume signal, a differential processing unit to differentiate the envelope with respect to a cuff pressure, a maximum value extracting unit to extract a maximum value of a differential value of the envelope, and a blood pressure decision unit that decides the cuff pressure used for the differential of the maximum value as a blood pressure.

12 Claims, 15 Drawing Sheets

(51) Int. Cl.
*A61B 5/00* (2006.01)
*A61B 5/026* (2006.01)

(56) References Cited

U.S. PATENT DOCUMENTS

| | | | | |
|---|---|---|---|---|
| 4,793,360 | A | * | 12/1988 | Miyawaki et al. ............ 600/494 |
| 5,309,916 | A | | 5/1994 | Hatschek |
| 5,323,782 | A | * | 6/1994 | Shirasaki et al. ............. 600/493 |
| 5,522,395 | A | * | 6/1996 | Shirasaki et al. ............. 600/495 |
| 5,651,369 | A | * | 7/1997 | Tomita ............................ 600/493 |
| 5,699,807 | A | | 12/1997 | Motogi et al. |
| 2002/0120199 | A1 | * | 8/2002 | Ogura et al. ................. 600/485 |
| 2003/0045801 | A1 | * | 3/2003 | Chen et al. ................... 600/494 |
| 2003/0097074 | A1 | * | 5/2003 | Oka et al. ..................... 600/490 |
| 2003/0098022 | A1 | | 5/2003 | Nakao et al. |
| 2004/0181157 | A1 | * | 9/2004 | Medero et al. ............... 600/500 |
| 2005/0119578 | A1 | * | 6/2005 | Kubo .............................. 600/490 |
| 2005/0256412 | A1 | * | 11/2005 | Shimazu et al. .............. 600/500 |
| 2006/0224068 | A1 | * | 10/2006 | Nunome ....................... 600/485 |
| 2008/0243008 | A1 | * | 10/2008 | Habu et al. ................... 600/494 |
| 2009/0312651 | A1 | * | 12/2009 | Sano et al. .................... 600/493 |
| 2009/0312652 | A1 | * | 12/2009 | Yamakoshi et al. .......... 600/493 |
| 2010/0016682 | A1 | * | 1/2010 | Schluess et al. .............. 600/301 |
| 2010/0076328 | A1 | * | 3/2010 | Matsumura et al. .......... 600/500 |
| 2010/0217137 | A1 | * | 8/2010 | Kanai et al. .................. 600/500 |
| 2010/0249615 | A1 | * | 9/2010 | Kukita et al. ................. 600/490 |

FOREIGN PATENT DOCUMENTS

| | | |
|---|---|---|
| JP | 4-250135 A | 9/1992 |
| JP | 7-79801 B2 | 8/1995 |
| JP | 8-89485 A | 4/1996 |

OTHER PUBLICATIONS

International Search Report w/translation from PCT/JP2009/054856 dated Apr. 14, 2009 (6 pages).

Y. Kenichi; "Blood Presure Measurement by Finger Volume Pulse Wave" with English translation; The Research Institute of Applied Electricity, Hokkaido University; Medical Instrument, vol. 53, No. 11, Additional Vol.; Nov. 1, 1983; pp. 571-580 (34 pages).

Y. Sawnoi et al.; "Yoseki Shindoho ni yoru Saiko Saitei Ketsuatsu no Shinki Ketteiho" translated as "A new determination method of systolic and diastolic blood pressure based on volume oscillometric method"; Dai 47 Kai Nippon Seitaii Kogakukai Taikai Program Ronbunshu translated as Graduate School of Natural Science and Technology, Kanazawa University; May 8, 2008, PS1-3-2 (p. 340) with English translation (5 pages).

International Search Report w/translation from PCT/JP2009/055009 dated Jun. 16, 2009 (4 pages).

Patent Abstracts of Japan; Publication No. 08-089485 dated Apr. 9, 1996 (1 page).

Patent Abstracts of Japan; Publication No. 04-250135 dated Sep. 7, 1992 (1 page).

Patent Abstracts of Japan; Publication No. 03-081375 dated Apr. 5, 1991 (1 page).

* cited by examiner (a)

(b)

| Data | Volume data | Cuff pressure data |
|---|---|---|
| 1 | V(1) | P(1) |
| 2 | V(2) | P(2) |
| 3 | V(3) | P(3) |
| 4 | V(4) | P(4) |
| 5 | V(5) | P(5) |
| 6 | V(6) | P(6) |
| 7 | V(7) | P(7) |
| 8 | V(8) | P(8) |
| 9 | V(9) | P(9) |
| ⋮ | ⋮ | ⋮ |
| N | V(n) | P(n) |

831 832 833   83

BLOOD PRESSURE MEASUREMENT APPARATUS, RECORDING MEDIUM THAT RECORDS BLOOD PRESSURE DERIVATION PROGRAM, AND BLOOD PRESSURE DERIVATION METHOD

TECHNICAL FIELD

The present invention relates to a blood pressure measurement apparatus, a recording medium that records a blood pressure derivation program, and a blood pressure derivation method, and particularly to a blood pressure measurement apparatus capable of detecting an arterial volume and a cuff pressure, a recording medium that records a blood pressure derivation program for deriving a blood pressure based on a arterial volume and a cuff pressure, and a blood pressure derivation method.

BACKGROUND ART

The blood pressure is one of barometers to analyze circulatory diseases, and performing risk analysis based on the blood pressure is effective for prevention of cardiovascular diseases such as stroke, heart failure and cardiac infarction. Among these, early-morning high blood pressure, in which the blood pressure rises in the early morning, is linked to cardiac diseases, stroke, and the like. Furthermore, in the early-morning high blood pressure, it has been found that a symptom of rapid increase in the blood pressure in one to one and a half hours after awakening, which is called morning surge, has a cause-and-effect relationship with stroke.

Thus, there have been proposed various sphygmomanometers capable of automatically measuring a systolic blood pressure and a diastolic blood pressure.

For example, electronic sphygmomanometers for measuring the blood pressure by the oscillometric method (oscillation method) have been marketed. In such electronic sphygmomanometers, in a process in which a pressure inside an arm band (cuff) wound around a measurement site (cuff pressure) is increased to become higher than a systolic blood pressure, and then the cuff pressure is gradually decreased, volume change of an artery accompanying pulsation of the blood pressure is detected by a pressure sensor as oscillation of the cuff pressure (e.g., Japanese Examined Patent Publication No. H3-81375 (Patent Document 1)). The cuff pressure corresponding to a time point when a maximum amplitude value of a pulse wave is detected is decided as an average blood pressure. According to the oscillometric method, the systolic blood pressure and the diastolic blood pressure are calculated by applying a predetermined algorithym to the cuff pressure and the pulse wave amplitude.

Moreover, a blood pressure measurement method by a volume oscillometric method has also been proposed ("Indirect Measurement of Arterial Pressure Using Volume Pulsation in the Human Finger" by Kenichi Yamakoshi, The Japanese jounal of medical instrumentation published on Nov. 1, 1983, Vol. 53, No. 11, Separate vol. p. 24 to 28 (Non-Patent Document 1)). Specifically, a volume pulse wave sensor is provided in a cuff and in a process in which a cuff pressure is increased (or decreased), a volume pulse wave component ($\Delta V$) is measured and a maximum point of amplitude and a vanishment point (or appearance point) are detected. The cuff pressures corresponding to the respective detected points are calculated as an average blood pressure and a systolic blood pressure. According to the volume oscillometric method, a diastolic blood pressure is calculated by applying the average blood pressure and the systolic blood pressure to a predetermined calculating equation.

Patent Document 1: Japanese Examined Patent Publication No. H3-81375

Non-Patent Document 1: "Indirect Measurement of Arterial Pressure Using Volume Pulsation in the Human Finger" by Kenichi Yamakoshi, The Japanese jounal of medical instrumentation published on Nov. 1, 1983, Vol. 53, No. 11, Separate vol. p. 24 to 28

DISCLOSURE OF THE INVENTION

Problems to be Solved by the Invention

However, going back to a generation mechanism of the pulse wave amplitude in the oscillometric method, there has been clarified nothing but a fact that the cuff pressure at the point when the pulse wave amplitude becomes maximal during the decrease (or increase) of the cuff pressure is an average blood pressure.

Moreover, in the volume oscillometric method as well, only the systolic blood pressure and the average blood pressure can be decided, but the diastolic blood pressure cannot be decided precisely.

In order to solve the above-described problems, the present invention is achieved, and an object thereof is to provide a blood pressure measurement apparatus capable of precisely deriving blood pressure (a systolic blood pressure and a diastolic blood pressure) based on a cuff pressure and a generation mechanism of a pulse wave amplitude, a recording medium that records a blood pressure derivation program, and a blood pressure derivation method.

Means for Solving the Problems

A blood pressure measurement apparatus according to an aspect of this invention includes: a cuff to be wound around a predetermined physical site of a measured person; a pressure detector to detect a cuff pressure representing a pressure inside the cuff; a volume detector provided in the cuff to detect an arterial volume signal indicating a volume of an artery of the measured person; and a derivation control unit to perform derivation control to derive a blood pressure of the measured person, based on the cuff pressure and the arterial volume signal, the derivation control unit including: a first extraction unit to extract an envelope of a volume pulse wave based on the arterial volume signal; a differential unit to differentiate the envelope with respect to the cuff pressure; a second extraction unit to extract a maximum value of a differential value of the envelope; and a decision unit to decide a blood pressure based on the cuff pressure used for the differential of the maximum value.

Preferably, further included are: an adjustment unit to adjust the pressure inside the cuff; and a drive control unit to control driving of the adjustment unit. The derivation control unit performs the derivation control when the cuff pressure is being decreased or increased at a constant rate by the drive control unit.

Preferably, the envelope includes a volume minimum point envelope in contact with arterial volume minimum points of respective pulse wave components included in the volume pulse wave, the differential unit differentiates the volume minimum point envelope, the second extraction unit extracts a maximum value of a differential value of the volume minimum point envelope, and the decision unit decides, as a diastolic blood pressure, the cuff pressure used for the differential of the maximum value.

Preferably, the envelope includes a volume maximum point envelope in contact with arterial volume maximum points of the respective pulse wave components included in the volume pulse wave, the differential unit differentiates the volume maximum point envelope, the second extraction unit extracts a maximum value of a differential value of the volume maximum point envelope, and the decision unit decides, as a systolic blood pressure, the cuff pressure used for the differential of the maximum value.

Preferably, further included are: an adjustment unit to adjust the pressure inside the cuff; and a drive control unit to control driving of the adjustment unit. The derivation control unit performs the derivation control when the cuff pressure is controlled so as to be decreased or increased in stages by a predetermined pressure difference by the drive control unit, and the decision unit decides the blood pressure by correcting the cuff pressure used for the differential of the maximum value.

Preferably, the envelope includes a volume minimum point envelope in contact with arterial volume minimum points of respective pulse wave components included in the volume pulse wave, the differential unit differentiates the volume minimum point envelope, the second extraction unit extracts a maximum value of a differential value of the volume minimum point envelope and differential values before and after the maximum value, and the decision unit decides a diastolic blood pressure by correcting the cuff pressure used for the differential of the maximum value based on the maximum value, the differential values before and after the maximum value, and the pressure difference.

Preferably, the envelope includes a volume maximum point envelope in contact with arterial volume maximum points of respective pulse wave components included in the volume pulse wave, the differential unit differentiates the volume maximum point envelope, the second extraction unit extracts a maximum value of a differential value of the volume maximum point envelope and differential values before and after the maximum value, and the decision unit decides a systolic blood pressure by correcting the cuff pressure used for the differential of the maximum value based on the maximum value, the differential values before and after the maximum value, and the pressure difference.

Preferably, the volume detector includes: a light emitting element to emit light to the artery; and a light receiving element to receive light transmitted through or light reflected at the artery of the light emitted by the light emitting element.

Preferably, the volume detector includes a plurality of electrodes to detect impedance of a site including the artery.

A recording medium according to another aspect of this invention records a blood pressure derivation program. The blood pressure derivation program causes an information processing apparatus to execute the steps of: extracting an envelope of a volume pulse wave based on arterial volume data; differentiating the envelope with respect to a cuff pressure based on cuff pressure data; extracting a maximum value of a differential value of the envelope; and deciding a blood pressure based on the cuff pressure used for the differential of the maximum value.

A blood pressure derivation method according to still another aspect of this invention is executed in an information processing apparatus including a storage unit that stores arterial volume data and cuff pressure data in chronological order, and an arithmetic operation processing unit, the method including the steps of: extracting an envelope of a volume pulse wave based on the arterial volume data by the arithmetic operation processing unit; differentiating the envelope with respect to a cuff pressure based on the cuff pressure data by the arithmetic operation processing unit; extracting a maximum value of a differential value of the envelope by the arithmetic operation processing unit; and deciding a blood pressure based on the cuff pressure used for the differential of the maximum value by the arithmetic operation processing unit.

Effect of the Invention

According to the present invention, the blood pressure can be precisely derived based on the cuff pressure and the generation mechanism of the pulse wave amplitude.

Figure 1:
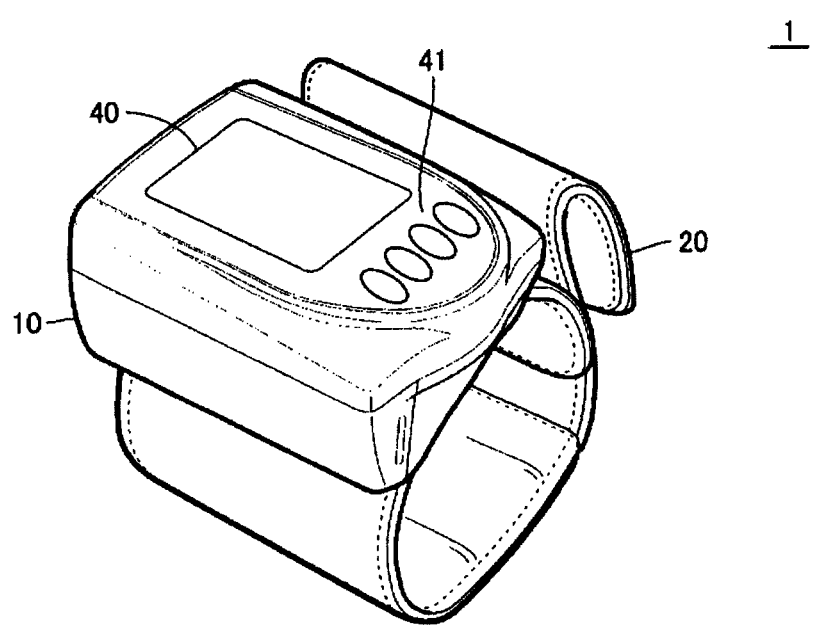
FIG. 1 is an external perspective diagram of a blood pressure measurement apparatus according to an embodiment of the present invention.

DESCRIPTION OF SYMBOLS 1 sphygmomanometer
10 main body portion 20 cuff
21 air bladder
30 air system
31 air tube
32 pressure sensor
33 oscillation circuit
40 display unit
41 operation unit
41A power switch
41B measurement switch
41C stop switch
41D memory switch
42 memory unit
43 flash memory
44 power supply
45 timing unit
46 interface unit
51 pump
52 valve
53 pump drive circuit
54 valve drive circuit
70 arterial volume sensor
71 light emitting element
72 light receiving element
73 light emitting element drive circuit
74 arterial volume detection circuit
80 measurement data
100, 210 CPU
101 drive control unit
102 volume signal detection processing unit
103 cuff pressure acquiring unit
104 derivation control unit
106, 106A storage processing unit
108, 1108 display control unit
113, 1113 envelope extracting unit
114, 1114 differential processing unit
115, 1115 maximum value extracting unit
116, 1116 blood pressure decision unit
132 recording medium
200 information processing apparatus
210 information processing apparatus body
212 memory
213 fixed disk
214 FD drive device
215 CD-ROM drive device
216 Interface unit
220 monitor
230 keyboard
240 mouse

BEST MODE FOR CARRYING OUT THE INVENTION

An embodiment of the present invention is described in detail with reference to the drawings. The same or corresponding portions in the figures are labeled with the same symbols, and descriptions thereof will not be repeated.

Embodiment

Outer Appearance and Configuration

Described first are an outer appearance and a configuration of a blood pressure measurement apparatus (hereinafter, simply referred to as a "sphygmomanometer") 1 according to the embodiment of the present invention.

Referring to FIG. 1, the sphygmomanometer 1 includes a main body portion 10, and a cuff 20 that can be wound around a wrist of a measured person. The main body portion 10 is mounted on the cuff 20. Arranged in a surface of the main body portion 10 are a display unit 40 made of, for example, liquid crystal or the like, and an operation unit 41 to receive an instruction from a user (measured person). The operation unit 41 includes a plurality of switches.

In the present embodiment, the cuff 20 is described on the assumption that it is worn on the wrist of the measured person. However, a site where the cuff 20 is worn (measurement site) is not limited to the wrist, but for example, it may be an upper arm.

As to the sphygmomanometer 1 according to the present embodiment, a form in which the main body portion 10 is mounted on the cuff 20, as shown in FIG. 1, is described as one example. However, as in an upper-arm type sphygmomanometer, there may be alternatively employed a form in which the main body portion 10 and the cuff 20 are connected by an air tube (air tube 31 in FIG. 2).

In a principle of the blood pressure measurement by the oscillometric method conventionally employed, a systolic blood pressure and a diastolic blood pressure cannot be derived precisely, as described above. Thus, various algorithms have been developed so far. However, since none of these algorithms is based on a generation mechanism of a pulse wave amplitude in the oscillometric method, measurement errors may occur to some measured persons.

Moreover, in the oscillometric method, information (volume change) that is generated by transmitting volume change of an artery to the cuff through a biological body is detected as oscillation of the cuff pressure. Generally, even when the same volume change is transmitted to the cuff, a level of the cuff pressure oscillation by the volume change of the cuff may be detected differently, depending on properties of outer cloth and an air bladder forming the cuff. Specifically, the level of the cuff pressure oscillation may be detected differently, depending on factors such as the cuff pressure, a way to wind the cuff, and a volume of the air bladder dependent on a circumferential length of a measurement site. Moreover, since the volume change of the artery is transmitted to the cuff through the biological body, the transmission of the arterial volume differs, depending on biological characteristics of the measurement site (an amount of muscle and cellulite, and elements such as tendon and bone). These factors contribute to the measurement error.

In view of the above, the sphygmomanometer 1 according to the present embodiment decides (measures) a blood pressure based on the dynamic properties of the artery, which is the generation mechanism of the pulse wave amplitude.

Figure 15:
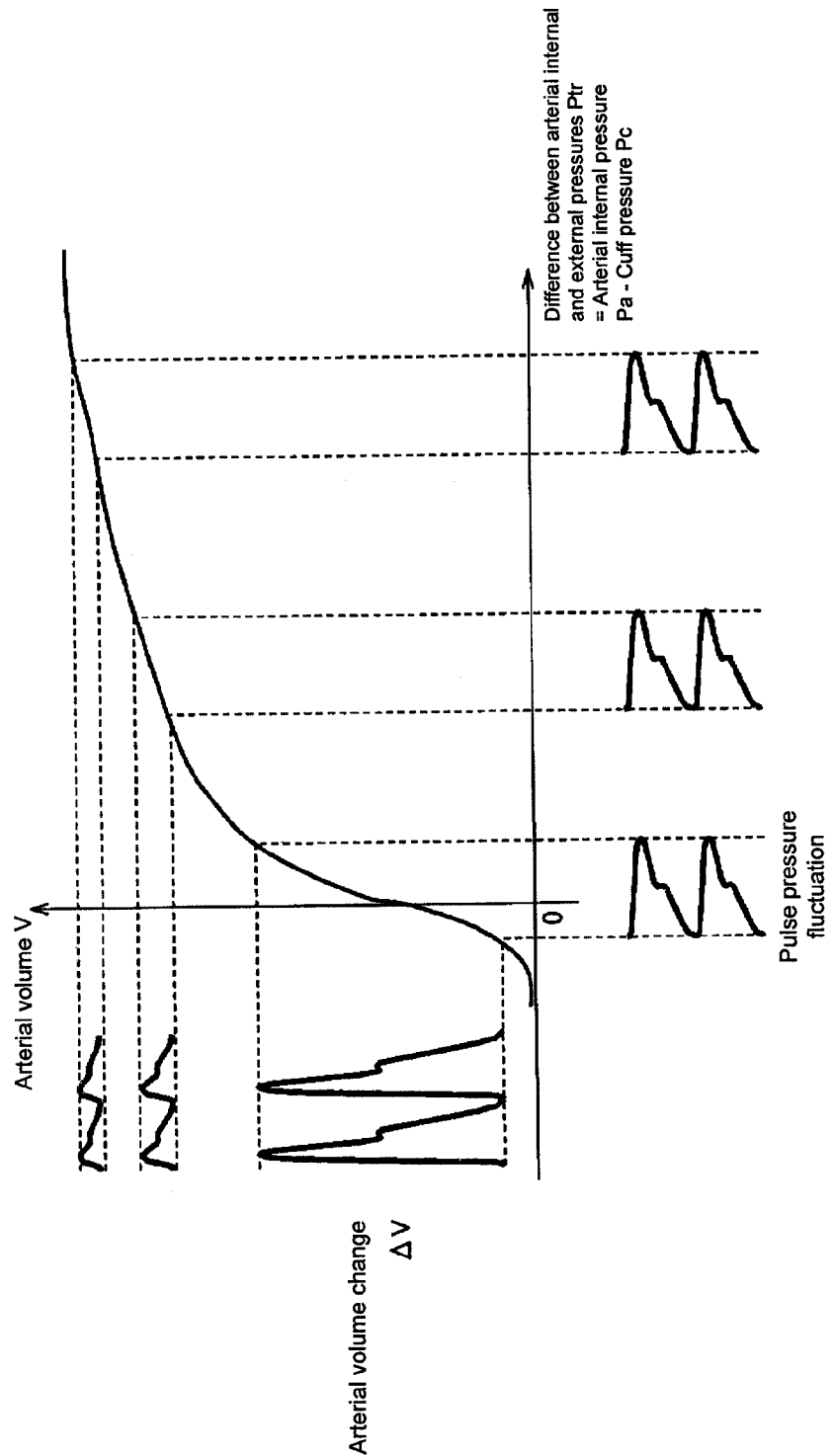
FIG. 15 is a graph showing dynamic properties of an artery.

FIG. 15 is a graph showing dynamic properties of an artery. In the graph of FIG. 15, a horizontal axis indicates a difference between internal and external pressures Ptr, and a vertical axis indicates an arterial volume V to show a relationship between the difference between the internal and external pressures Ptr and the arterial volume V. The difference between the internal and external pressures Ptr indicates a difference between an arterial internal pressure Pa and a cuff pressure Pc applied to the cuff from the outside of the biological body.

As shown in this graph, the dynamic properties of the artery generally exhibit strong nonlinearity, and when the difference between the internal and external pressures Ptr is 0, that is, when an arterial wall is in an unloaded state, compliance of the artery becomes maximal, and the volume change corresponding to pulse pressure fluctuation becomes maximal.

From the foregoing, it is understood that when the arterial volume is detected in a process of increasing or decreasing the cuff pressure and the arterial volume is differentiated with respect to the cuff pressure, the cuff pressure at which a maximum value is obtained coincides with the arterial internal pressure.

The sphygmomanometer 1 according to the present embodiment utilizes the fact that at a point when the arterial wall enters the unloaded state, the value of the differentiation result becomes maximal, to decide the systolic blood pressure and the diastolic blood pressure.

Figure 2:
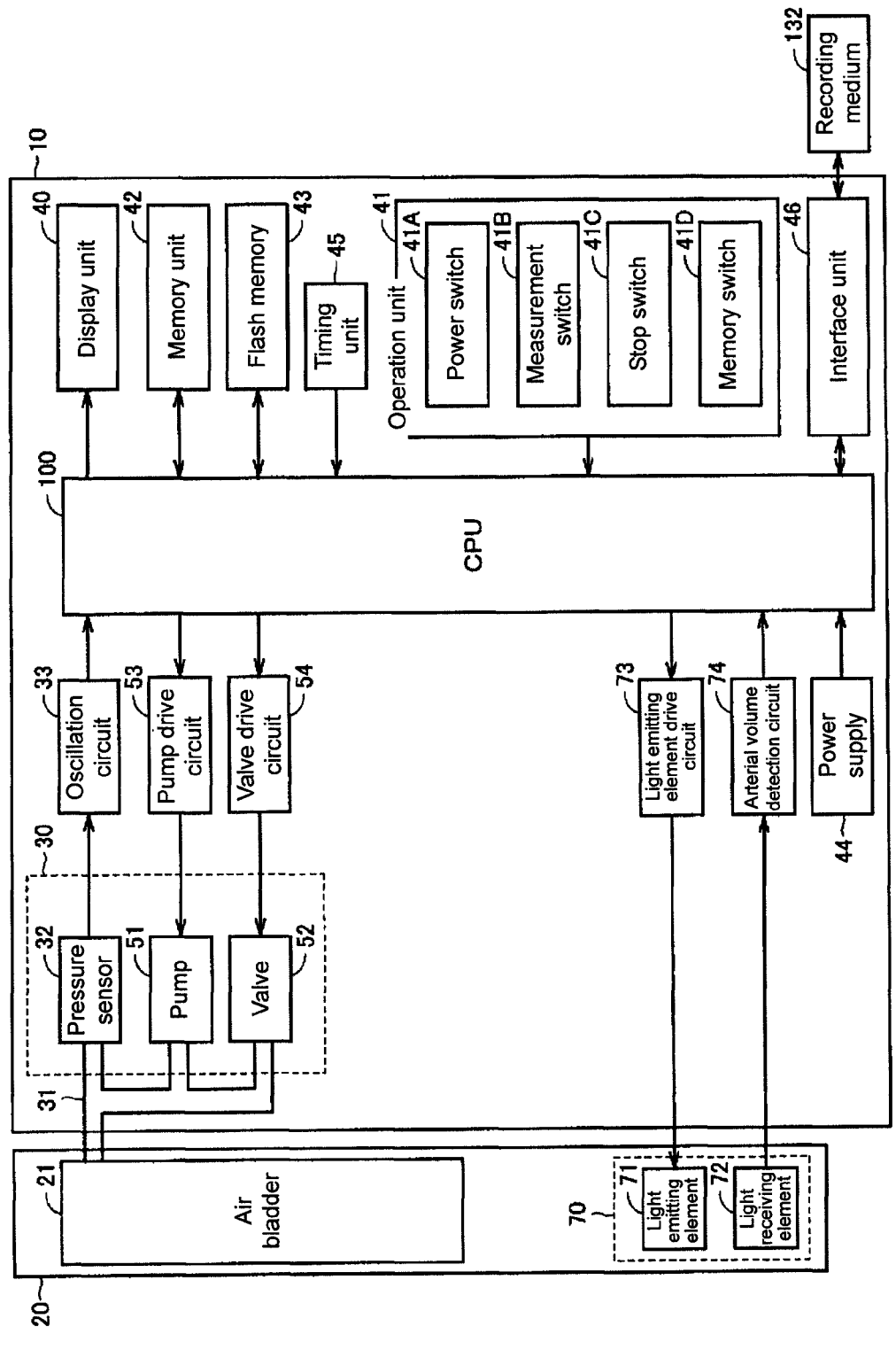
FIG. 2 is a block diagram representing a hardware configuration of the blood pressure measurement apparatus according to the embodiment of the present invention.

Referring to FIG. 2, the cuff 20 of the sphygmomanometer 1 includes an air bladder 21 and an arterial volume sensor 70. The arterial volume sensor 70 has light emitting elements 71 and light receiving elements 72. The light emitting elements 71 emit light to an artery, and the light receiving elements 72 receive light (transmitted light) emitted by the light emitting elements 71 and transmitting through the artery, or light (reflected light) that is reflected by the artery. The light emitting elements 71 and the light receiving elements 72 are arranged at predetermined intervals inside the air bladder 21.

The arterial volume sensor 70 only needs to detect a volume of an artery, and may detect the volume of the artery by impedance. In this case, in place of the light emitting elements 71 and the light receiving elements 72, there are included a plurality of electrodes to detect an impedance of a site including the artery.

The air bladder 21 is connected to an air system 30 through the air tube 31.

The main body portion 10 includes, in addition to the above-described display unit 40 and the operation unit 41, the air system 30, a CPU (Central Processing Unit) 100 to intensively control respective units and perform various arithmetic operations, a memory unit 42 to store programs that cause the CPU 100 to perform predetermined operations and various type of data, a nonvolatile memory (e.g., flash memory) 43 to store a measured blood pressure, a power supply 44 to supply power to the CPU 100, a timing unit 45 that performs timing operations, and an interface unit 46 to read and write programs and data from and onto a detachable recording medium 132.

The operation unit 41 has a power switch 41A that receives input of an instruction to power on or off, a measurement switch 41B to receive an instruction of measurement start, a stop switch 41C to receive an instruction of measurement stop, and a memory switch 41D to receive an instruction to read information such as the blood pressure recorded on the flash memory 43.

The air system 30 includes a pressure sensor 32 to detect a pressure (cuff pressure) inside the air bladder 21, a pump 51 to supply air to the air bladder 21 to increase the cuff pressure, and a valve 52 opened or closed to exhaust or fill the air from and into the air bladder 21.

The main body portion 10 further includes a light emitting element drive circuit 73, an arterial volume detection circuit 74, and an oscillation circuit 33, a pump drive circuit 53, and a valve drive circuit 54 in connection with the above-described air system 30.

The light emitting element drive circuit 73 causes the light emitting elements 71 to emit light at predetermined timing in accordance with an instruction signal from the CPU 100. The arterial volume detection circuit 74 converts output from the light receiving elements 72 to a voltage value to thereby sense the arterial volume.

The pressure sensor 32 is, for example, a capacitance type pressure sensor, in which a volume value is changed in accordance with the cuff pressure. The oscillation circuit 33 outputs a signal of an oscillation frequency in accordance with the volume value of the pressure sensor 32 to the CPU 100. The CPU 100 senses a pressure by converting the signal obtained from the oscillation circuit 33 to the pressure. The pump drive circuit 53 controls the driving of the pump 51 based on a control signal given from the CPU 100. The valve drive circuit 54 performs the opening and closing control of the valve 52 based on a control signal given from the CPU 100.

Although the cuff 20 includes the air bladder 21, fluid supplied to the cuff 20 is not limited to air, but for example, liquid or gel may be employed. Alternatively, not limited to fluid, but uniform particles such as micro beads may be employed.

Figure 3:
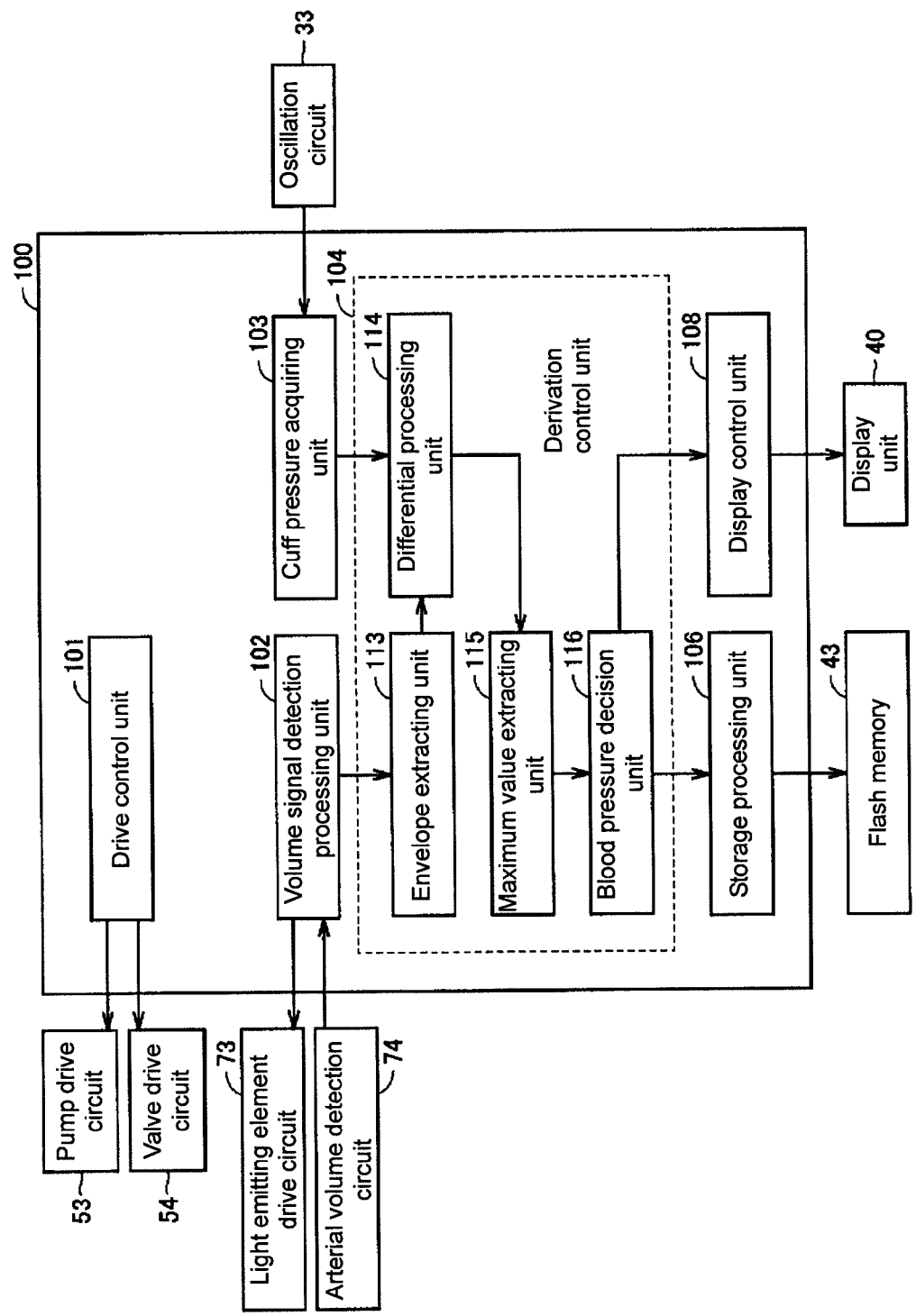
FIG. 3 is a functional block diagram showing a functional configuration of the blood pressure measurement apparatus according to the embodiment of the present invention.

Referring to FIG. 3, the CPU 100 includes, as functions thereof, a drive control unit 101, a volume signal detection processing unit 102, a cuff pressure acquiring unit 103, a derivation control unit 104 that performs control to derive the blood pressure of the measured person, a storage processing unit 106, and a display control unit 108. Shown in FIG. 3 is only hardware directly communicating the signals and the data with these functional blocks.

The drive control unit 101 transmits the control signals to the pump drive circuit 53 and the valve drive circuit 54 in order to adjust the cuff pressure. Specifically, control is performed so as to increase the cuff pressure up to a predetermined value and gradually decrease the cuff pressure. In the present embodiment, in the process of decreasing the cuff pressure at a constant rate, blood pressure derivation processing is performed by the derivation control unit 104. The blood pressure derivation processing may be alternatively performed in the process of gradually increasing the cuff pressure.

The derivation control unit 104 has an envelope extracting unit 113, a differential processing unit 114, a maximum value extracting unit 115, and a blood pressure decision unit 116.

The volume signal detection processing unit 102 transmits a control signal to the light emitting element drive circuit 73 so as to drive the light emitting elements 71 at the predetermined timing in parallel to the decrease of the cuff pressure by the drive control unit 101. Moreover, the volume signal detection processing unit 102 continuously detects an arterial volume signal from the arterial volume detection circuit 74, and acquires a volume pulse wave. The volume of the artery is changed by the pulsation of the blood pressure. In the present embodiment, the "volume pulse wave" is a curve indicating change of the arterial volume that appears in accordance with the cuff pressure, and is indicated by a waveform PG of FIG. 4, for example.

The volume pulse wave detected by the volume signal detection processing unit 102 is outputted to the envelope extracting unit 113.

The cuff pressure acquiring unit 103 converts the signal obtained from the oscillation circuit 33 to a pressure to continuously acquire the pressure in parallel to the control by the drive control unit 101. The acquired cuff pressure is outputted to the differential processing unit 114. The cuff pressure is also outputted to the drive control unit 101.

Figure 4:
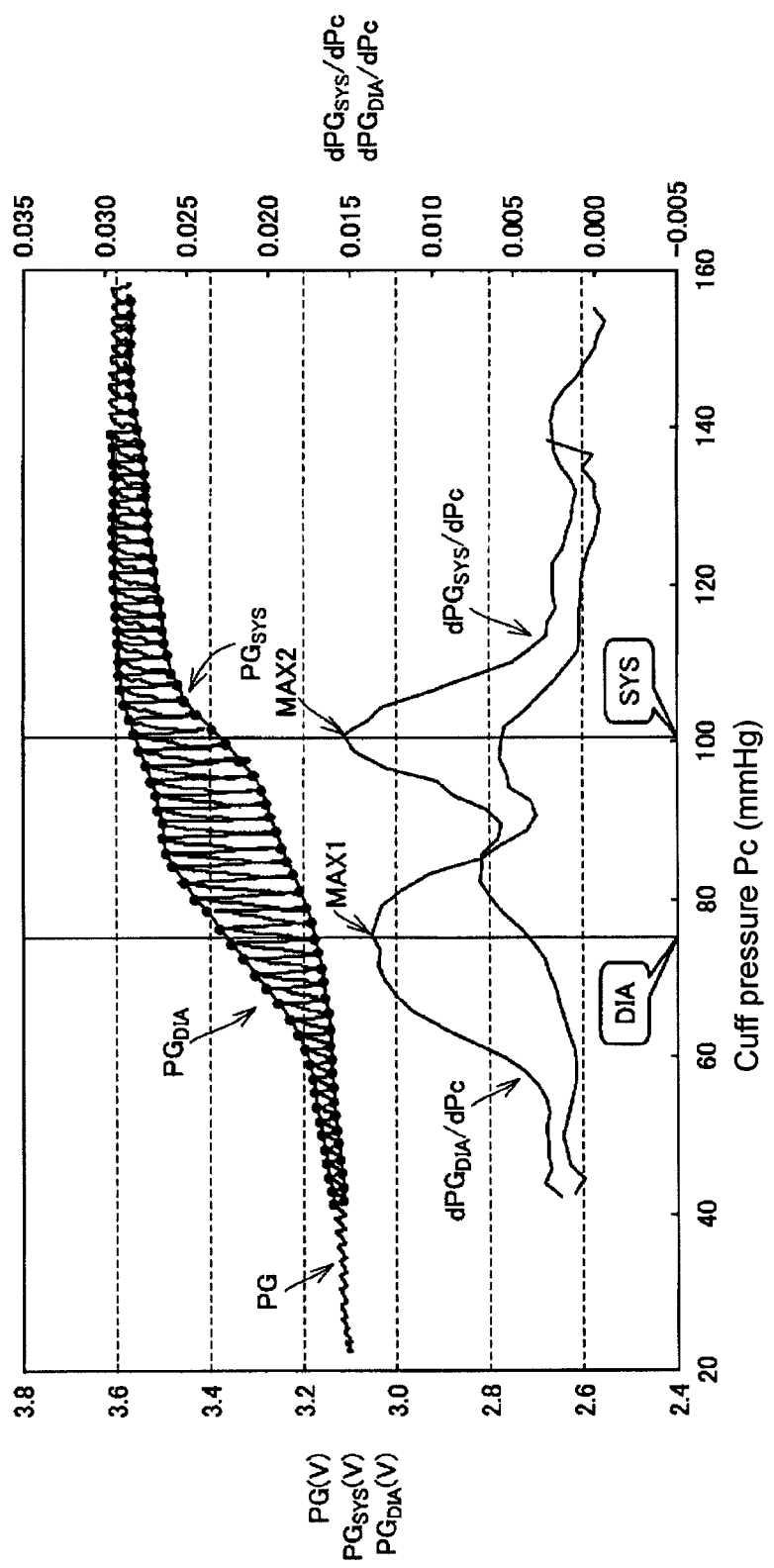
FIG. 4 is a graph showing a volume pulse wave and differential curves during increasing pressure.

In order to describe the function of the derivation control unit 104, FIG. 4 is further referred to.

FIG. 4 is a graph showing the volume pulse wave and differential curves (to be described later) during increasing the pressure.

The envelope extracting unit 113 extracts envelopes of the volume pulse wave detected by the volume signal detection processing unit 102. More specifically, extracted are a volume minimum point envelope in contact with arterial volume minimum points of respective pulse wave components composing the volume pulse wave, and a volume maximum point envelope in contact with arterial volume maximum points of the respective pulse wave components. Each of the "pulse wave components" herein corresponds to the change of the arterial volume in each pulse of the pulsations.

In the present embodiment, a property that near infrared rays entering the biological body are absorbed by hemoglobin in the artery is utilized to detect the arterial volume. When the volume of the artery is large, the amount of hemoglobin is large, and thus, the amount of received light is small. On the contrary, when the volume of the artery is small, the amount of hemoglobin is small, and thus, the amount of received light is large.

Therefore, a line (volume minimum point envelope) $PG_{DIA}$ connecting the maximum points of the pulse wave components of the volume pulse wave (i.e., points where the arterial volume is minimal) indicates the arterial volume at the time of the diastolic blood pressure, and on the contrary, a line (volume maximum point envelope) $PG_{SYS}$ connecting the minimum points (points where the arterial volume is maximal) indicates the arterial volume at the time of the systolic blood pressure.

Information of the extracted envelopes is outputted to the differential processing unit 114.

The differential processing unit 114 differentiates the envelopes extracted by the envelope extracting unit 113 with respect to the cuff pressures acquired by the cuff pressure acquiring unit 103. Specifically, the differential processing unit 114 differentiates the volume minimum point envelope $PG_{DIA}$ and the volume maximum point envelope $PG_{SYS}$ with respect to the cuff pressure to thereby calculate respective differential values. In the following description, the differential value of the former is also referred to as a first differential value, and the differential value of the latter is also referred to as a second differential value. In FIG. 4, a waveform obtained by connecting the first differential values is indicated by $dPG_{DIA}/dPc$. A waveform obtained by connecting the second differential values is indicated by $dPG_{SYS}/dPc$. In the present embodiment, these waveforms are referred to as differential curves.

The calculated first and second differential values are outputted to the maximum value extracting unit 115.

The maximum value extracting unit 115 extracts maximum values of the differential values of the envelopes, that is, maximum values of the differential curves (peaks). Referring to FIG. 4, specifically, the maximum value extracting unit 115 extracts differential maximum values MAX1 and MAX2 for the first differential value and the second differential value, respectively. Information of the respective extracted differential maximum values is outputted to the blood pressure decision unit 116.

The blood pressure decision unit 116 decides the blood pressure based on the cuff pressures corresponding to the differential maximum values (i.e., cuff pressures used for the differentiation of the differential maximum values). Hereinafter, each of the above-described cuff pressures is also referred to as a "specific cuff pressure".

Referring to FIG. 4, specifically, the blood pressure decision unit 116 decides the cuff pressure corresponding to the maximum value MAX1 of the first differential value as a diastolic blood pressure DIA. Moreover, it decides the cuff pressure corresponding to the maximum value MAX 2 of the second differential value as a systolic blood pressure SYS. Information of the decided blood pressures is outputted to the storage processing unit 106 and the display control unit 108.

The storage processing unit 106 stores the blood pressures (the diastolic blood pressure and the systolic blood pressure) decided by the blood pressure decision unit 116, in the flash memory 43 in association with a measurement date and time. This allows measurement data in which blood pressure data and date and time data are associated with each other to be recorded on the flash memory 43 at each measurement.

The display control unit 108 performs control to display, on the display unit 40, the blood pressures (the diastolic pressure and the systolic pressure) decided by the blood pressure decision unit 116. This allows the blood pressures of the measured person on the display unit 40.

The operations of the respective functional blocks included in the CPU 100 may be realized by executing software stored in the memory unit 42, or at least one of these functional blocks may be realized as hardware.

Alternatively, at least one of the blocks described as hardware (circuits) may be realized by the CPU 100 executing software stored in the memory unit 42.

<Operation>

Described next is operation of the sphygmomanometer 1 in the present embodiment.

Figure 5:
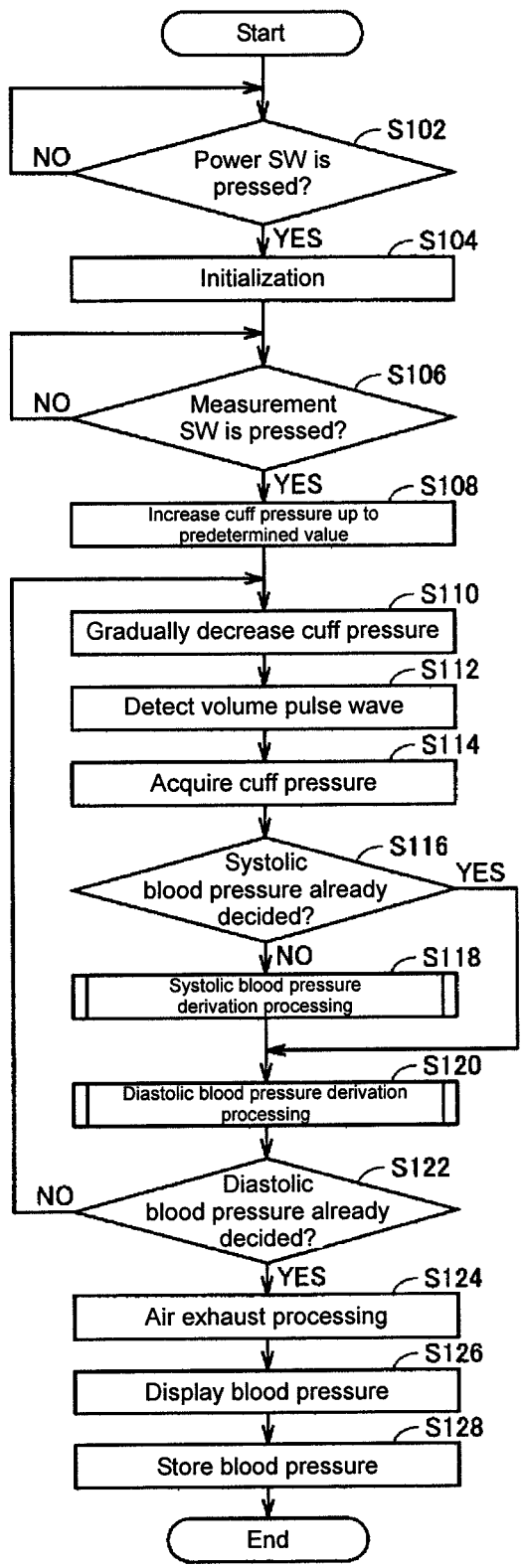
FIG. 5 is a flowchart showing blood pressure measurement processing that is executed by the blood pressure measurement apparatus in the embodiment of the present invention.

FIG. 5 is a flowchart showing blood pressure measurement processing executed by the sphygmomanometer in the embodiment of the present invention. The processing shown in the flowchart of FIG. 5 is stored in advance in the memory unit 42 as a program, and the CPU 100 reads and executes this program to thereby realize the function of the blood pressure measurement processing.

Referring to FIG. 5, the CPU 100 first determines whether or not the power switch 41A has been pressed (step S102). The CPU 100 stands by until the power switch 41A is pressed (NO in step S102). If the CPU 100 determines that the power switch 41A has been pressed (YES in step S102), the processing goes to step S104.

In step S104, the CPU 100 performs initialization processing. Specifically, a predetermined area of the memory unit 42 is initialized, the air in the air bladder 21 is exhausted, and correction of the pressure sensor 32 is performed.

Next, the CPU 100 determines whether or not the measurement switch 41B has been pressed (step S106). The CPU 100 stands by until the measurement switch 41B is pressed (NO in step S106). If the CPU 100 determines that the measurement switch 41B has been pressed (YES in step S106), the processing goes to step S108.

In step S108, the drive control unit 101 performs processing of controlling the pump drive circuit 53 and the valve drive circuit 54 to increase the cuff pressure up to the predetermined value. Specifically, the valve 52 is closed to gradually increase the cuff pressure up to the predetermined value by the pump 51. Here, the predetermined value is a pressure value set in advance. However, instead, it may be pulse wave information detected during increasing the pressure, or a pressure value decided based on calculated blood pressure values and the number of pulses. Alternatively, the pressure may be continuously increased while the user (measured person) continues to press the measurement switch 41B.

Subsequently, the drive control unit 101 performs the processing of gradually decreasing the cuff pressure (step S110). Specifically, the pump 51 is stopped to control an opening amount of the valve 52, so that the cuff pressure is gradually decreased.

In parallel to the processing in step s110, the volume signal detection processing unit 102 detects the arterial volume based on the signal from the arterial volume detection circuit 74. The detected arterial volume is recorded on a predetermined area of the memory unit 42 in chronological order (step S112). Thereby, the volume pulse wave is obtained.

Subsequently, the cuff pressure acquiring unit 103 acquires the cuff pressure based on the signal from the oscillation circuit 33. The acquired cuff pressure is recorded on a predetermined area of the memory unit 42 in chronological order (step S114).

The processing in step S112 and the processing in step S114 may be performed in parallel.

In the present embodiment, the blood pressure derivation processing is executed in real time. Accordingly, the following processing from steps S116 to S120 is also executed in parallel to the cuff pressure decrease processing.

In step S116, the derivation control unit 104 determines whether or not the systolic pressure has been already decided. If it is determined that the systolic blood pressure has not yet been decided (NO in step S116), the processing goes to step S118. On the other hand, if it is determined that the systolic blood pressure has been already decided (YES in step S116), the processing goes to step S120.

In step S118, the derivation control unit 104 executes systolic blood pressure derivation processing. This systolic blood pressure derivation processing will be described in detail later, using a subroutine shown in FIG. 7.

In step S120, the derivation control unit 104 executes diastolic blood pressure derivation processing. This diastolic blood pressure derivation processing will be described in detail later, using a subroutine shown in FIG. 6.

The diastolic blood pressure derivation processing and the systolic blood pressure derivation processing may be executed in parallel.

Next, the derivation control unit 104 determines whether or not the diastolic blood pressure has been already decided (step S122). If it is determined that the diastolic blood pressure has not yet been decided (NO in step S122), the processing returns to step S110 to repeat the above-described processing.

On the other hand, if it is determined that the diastolic blood pressure has been already decided (YES in step S122), the processing goes to step S124.

In step S124, the drive control unit 101 controls the valve drive circuit 54 to completely open the valve 52 and exhaust the air.

When the exhaust processing ends, the display control unit 108 displays the decided systolic blood pressure and diastolic blood pressure on the display unit 40 (step S126). Moreover, the storage processing unit 106 stores the decided systolic blood pressure and diastolic blood pressure on the flash memory 43 in association with the timing data from the timing unit 45 (step S128).

As described above, the blood pressure measurement processing in the present embodiment is ended.

Figure 6:
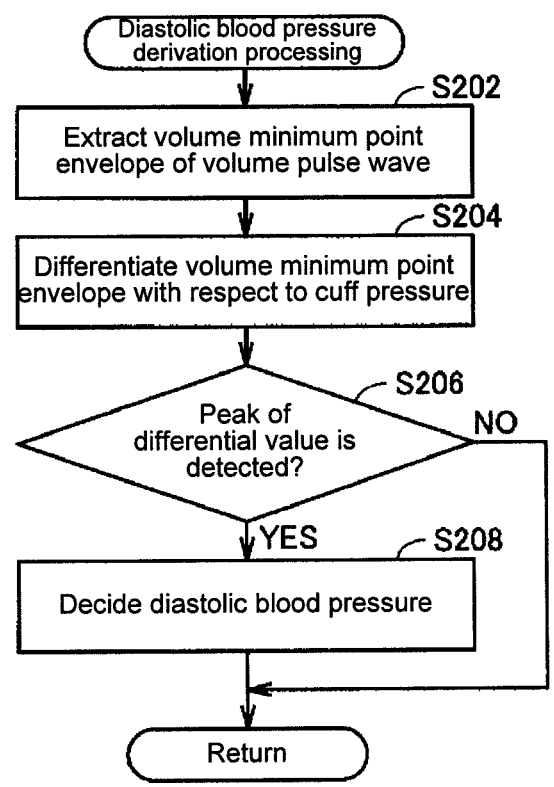
FIG. 6 is a flowchart showing diastolic blood pressure derivation processing in the embodiment of the present invention.

FIG. 6 is a flowchart showing the diastolic blood pressure derivation processing in the embodiment of the present invention.

Referring to FIG. 6, the envelope extracting unit 113 extracts the volume minimum point envelope of the volume pulse wave (step S202). The processing is returned to the main routine without performing the subsequent processing until the volume minimum point envelope is enabled to be extracted.

Next, the differential processing unit 114 differentiates the extracted volume minimum point envelope with respect to the cuff pressure (step S204). This cuff pressure is of the time point when the latest volume minimum point of the volume pulse wave is extracted.

The maximum value extracting unit 115 detects the peak of the differential value (step S206). If it is determined that the peak of the differential value has been detected (YES in step S206), the processing goes to step S208. On the other hand, if it is determined that the peak of the differential value has not been detected (NO in step S206), the processing is returned to the main routine.

In step S208, the blood pressure decision unit 116 decides the specific cuff pressure corresponding to the differential maximum value as the diastolic blood pressure, and temporarily records the same on the predetermined area of the memory unit 42. When the above processing ends, the processing is returned to the main routine.

Figure 7:
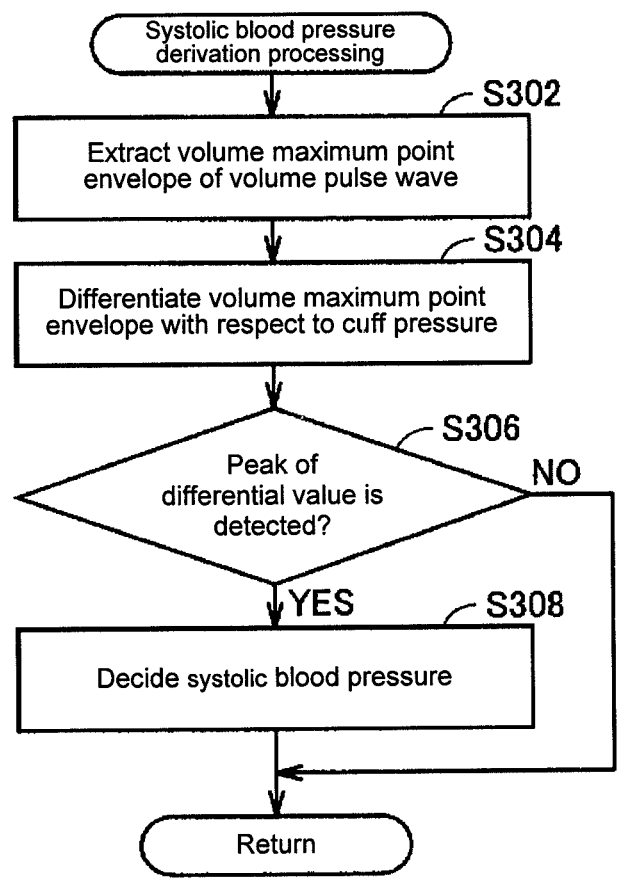
FIG. 7 is a flowchart showing systolic blood pressure derivation processing in the embodiment of the present invention.

FIG. 7 is a flowchart showing the systolic blood pressure derivation processing in the embodiment of the present invention.

Referring to FIG. 7, the envelope extracting unit 113 extracts the volume maximum point envelope of the volume pulse wave (step S302). The processing is returned to the main routine without performing the subsequent processing until the volume maximum point envelope is enabled to be extracted.

Next, the differential processing unit 114 differentiates the extracted volume maximum point envelope with respect to the cuff pressure (step S304). This cuff pressure is of the time point when the latest volume maximum point of the volume pulse wave is extracted.

The maximum value extracting unit 115 detects the peak of the differential value (step S306). If it is determined that the peak of the differential value has been detected (YES in step S306), the processing goes to step S308. On the other hand, if it is determined that the peak of the differential value has not been detected (NO in step S306), the processing is returned to the main routine.

In step S308, the blood pressure decision unit 116 decides the specific cuff pressure corresponding to the differential maximum value as the systolic blood pressure, and temporarily records the same on the predetermined area of the memory unit 42. When the above processing ends, the processing is returned to the main routine.

As described above, in the blood pressure decision method in the present embodiment, since the mechanism of blood pressure decision is based on the volume change of the artery, the blood pressure can be decided precisely. Particularly, the diastolic blood pressure, which is difficult to decide in the conventional oscillometric method and the volume oscillation method, can also be decided easily and precisely.

<Display Example and Measurement Data Storage Example>

Figure 8:
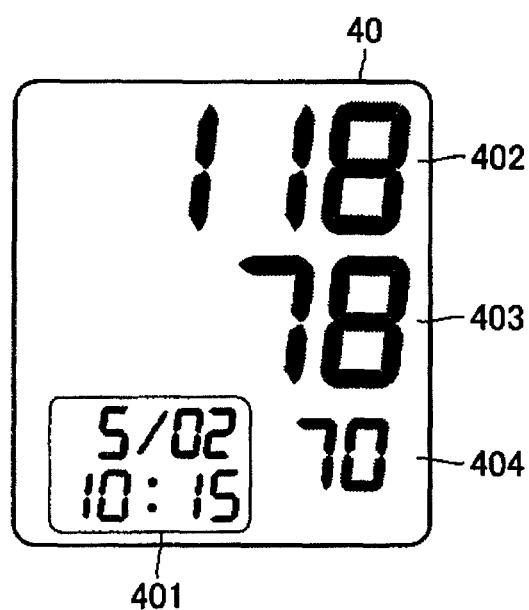
FIG. 8 is diagram showing one example of a screen displayed in step S126 of FIG. 5.

FIG. 8 is a diagram showing one example of a screen displayed in step S126 of FIG. 5.

Referring to FIG. 8, the measurement date and time are displayed in an area 401 of the display unit 40. The measurement date and time, for example, correspond to a time point when the measurement switch 41B is pressed. The systolic blood pressure decided in step S308 of FIG. 7 is displayed in an area 402 of the display unit 40. The diastolic blood pressure decided in step S208 of FIG. 6 is displayed in an area 403 of the display unit 40. Moreover, the number of pulses calculated by a publicly known technique is displayed in an area 404 of the display unit 40.

Figure 9:
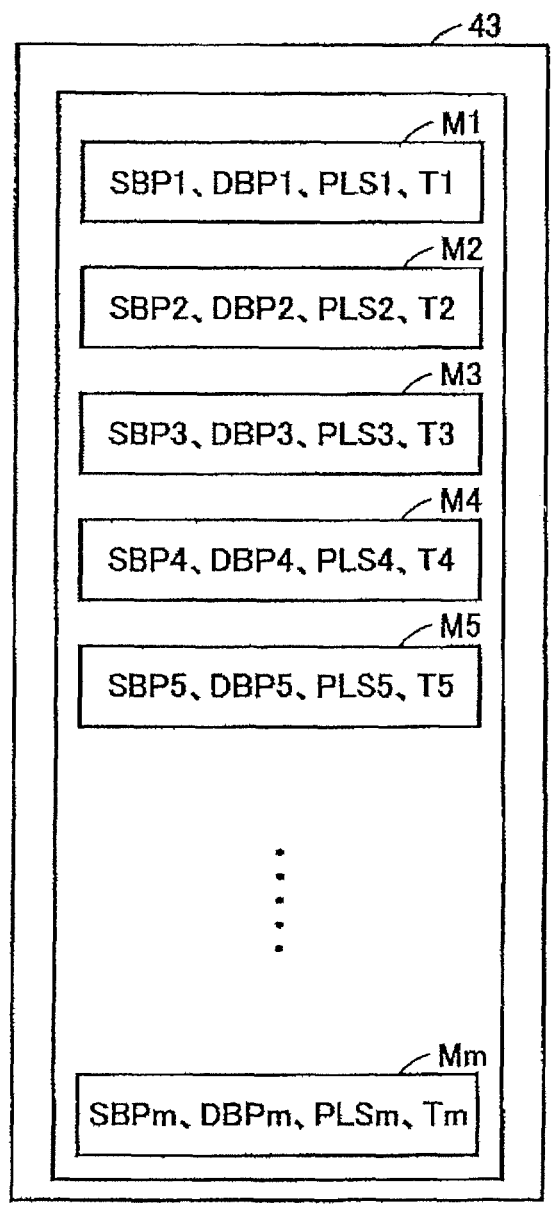
FIG. 9 is a diagram showing one example of a data structure of measurement data.

FIG. 9 is a diagram showing one example of a data structure of the measurement data.

Referring to FIG. 9, records in each of which measurement value and the measurement date and time are associated with each other are stored as measurement data M1 to Mm (m=1, 2, 3, . . . ). In each piece of the measurement data, systolic blood pressure data SBP indicating the systolic blood pressure, diastolic blood pressure data DBP indicating the diastolic blood pressure, pulse number data PLS indicating the number of pulses, and measurement date and time data T are included. It is only needed to associate the measurement value and the measurement date and time with each other, and the data structure is not limited to the storage form using the records.

<Modification 1>

In the above-described embodiment, the blood pressure derivation processing is executed in real time in the process in which the cuff pressure is decreased. This allows the cuff pressure decrease processing to be halted at a time point when the blood pressure is decided, and as a result, time required for the blood pressure measurement can be shortened.

However, after the cuff pressure is decreased to the predetermined value (e.g., 20 mmHg), the blood pressure derivation processing may be executed. The operation of the sphygmomanometer 1 in this case is briefly described with reference to FIG. 10. The outer appearance and the configuration of the sphygmomanometer 1 are similar to those of the above-described embodiment.

Figure 10:
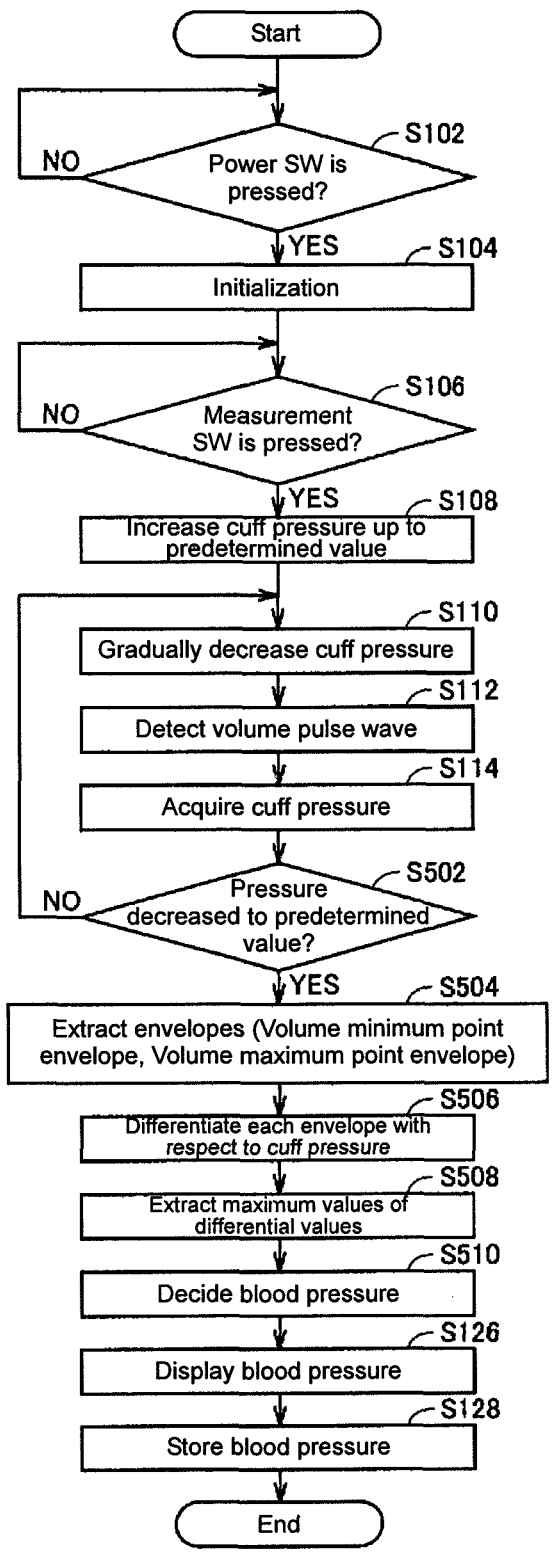
FIG. 10 is a flowchart showing blood pressure measurement processing in Modification 1 of the embodiment of the present invention.

FIG. 10 is a flowchart showing the blood pressure measurement processing in Modification 1 of the embodiment of the present invention. Similar pieces of the processing to those of the flowchart in FIG. 5 are labeled with the same step numbers. Accordingly, descriptions thereof will not be repeated.

As in the embodiment, the processing from steps S102 to S114 is executed. In Modification 1, the decrease processing in step S110, the volume signal detection processing in step S112, and the cuff pressure acquisition processing in step S114 are executed in parallel.

When the processing in step S114 ends, the drive control unit 101 determines whether or not the cuff pressure has been decreased to the predetermined value (e.g., 20 mmHg) (step S502). When it is determined that the cuff pressure has not been decreased to the predetermined value (NO in step S502), the processing returns to step S110. On the other hand, if the drive control unit 101 determines that the cuff pressure has been decreased to the predetermined value (YES in step S502), the processing goes to step S504.

In step S504, the envelope extracting unit 113 extracts the volume minimum point envelope and the volume maximum point envelope based on the arterial volume data (i.e., volume pulse wave data) and the cuff pressure data recorded on the memory unit 42 in chronological order in the above-described steps S112 and S114. Next, the differential processing unit 114 differentiates the respective envelopes with respect to the cuff pressure (step S506).

The maximum value extracting unit 115 extracts the maximum values of the respective differential values (step S508). The blood pressure decision unit 116 decides the specific cuff pressures corresponding to the extracted differential maximum values, as the systolic blood pressure and the diastolic blood pressure, respectively (step S510).

When the blood pressures are decided, as in the above-described embodiment, step S126 (display processing) and step S128 (storage processing) are executed.

As described above, the blood pressure measurement processing in the modification of the present embodiment is ended.

In this manner, in Modification 1 of the present embodiment as well, effects similar to those in the embodiment can be obtained.

<Modification 2>

In the above-described embodiment and Modification 1 thereof, in the process of gradually decreasing or increasing the cuff pressure, the arterial volume signal and the cuff pressure are detected. However, the arterial volume and the cuff pressure may be detected in a process in which the cuff pressure is decreased or increased in stages (i.e., by a predetermined pressure difference).

In this case, the blood pressure decision unit 116 can calculate the systolic blood pressure and the diastolic blood pressure by correcting the specific cuff pressures.

In Modification 2, the maximum value extracting unit 115, after extracting the maximum values MAX1 and MAX2 of the first and the second differential values, further extracts the differential values before and after the respective differential maximum values.

The blood pressure decision unit 116 corrects the specific pressure, based on the pressure differences between the differential maxim value MAX1 and the differential values before and after the same. Thereby, the diastolic blood pressure is decided. Moreover, the blood pressure decision unit 116 corrects the specific cuff pressure, based on the pressure differences between the differential maximum value MAX2 and the differential values before and after the same. Thereby, the systolic blood pressure is decided.

Specifically, for example, in the following manner, the diastolic blood pressure and the systolic blood pressure are decided.

(Correction of Diastolic Blood Pressure)

The maximum value MAX1 of the differential value $dPG_{DIA}/dPc$ of the volume pulse wave and the cuff pressure at this time are indicated as "$dPG_{DIA}/dPC(n)$" and "$Pc(n)$", respectively. The differential values before and after the maximum value MAX1 are indicated as "$dPG_{DIA}/dPc(n-1)$" and "$dPG_{DIA}/dPc(n+1)$", respectively.

A difference between the maximum value MAX1 and the differential value before the same (first difference), and a difference between the maximum value MAX1 and the differential value after the same (second difference) are indicated as "$\Delta dPG_{DIA}/dPc(n-1)$" and "$\Delta dPG_{DIA}/dPc(n+1)$", respectively. Then, the first and second differences are expressed by the following expressions (1), (2).

$$\Delta dPG_{DIA}/dPc(n-1) = dPG_{DIA}/dPc(n-1) - dPG_{DIA}/dPc \quad (1)$$

$$\Delta dPG_{DIA}/dPc(n+1) = dPG_{DIA}/dPc(n+1) - dPG_{DIA}/dPc \quad (2)$$

The blood pressure decision unit 116 corrects the specific cuff pressure by a larger value of the first difference ($\Delta dPG_{DIA}/dPc(n-1)$) and the second difference ($\Delta dPG_{DIA}/dPc(n+1)$).

When the first difference is larger than the second difference, the diastolic blood pressure ("DIA") is calculated by the following expression (3).

$$DIA = Pc(n) - \Delta dPG_{DIA}/dPc(n-1)/dPG_{DIA}/dPc(n) \times \Delta Pc \times \alpha \quad (3)$$

When the first difference is not larger than the second difference, the diastolic blood pressure is calculated by the following expression.

$$DIA = Pc(n) + \Delta dPG_{DIA}/dPc(n+1)/dPG_{DIA}/dPc(n) \times \Delta Pc \times \alpha \quad (4)$$

In the expressions (3) and (4), "$\Delta Pc$" indicates the pressure difference by which the pressure is increased or decreased in stages, and "$\alpha$" indicates a predetermined constant.

(Correction of Systolic Blood Pressure)

For the correction of the systolic blood pressure as well, similar processing to the correction of the diastolic blood pressure is executed. Description thereof is thus not repeated.

The blood pressure deciding processing in Modification 2 of the present embodiment may be executed in place of steps S208 in FIG. 6, S308 in FIG. 7, and S510 in FIG. 10.

<Modification 3>

While in the above-described embodiment and Modifications 1, 2, descriptions have been given on the assumption that entire the blood pressure measurement processing as described above is executed in the sphygmomanometer 1, the blood pressure derivation processing in the blood pressure measurement processing may be executed in a separate information processing apparatus (representatively, a personal computer). That is, in a blood pressure measurement system including the sphygmomanometer 1 and the information processing apparatus, the blood pressure measurement processing as described above may be realized.

Such a case is described as Modification 3.

In Modification 3, in the sphygmomanometer 1, the processing in steps S102 to S502 of the blood pressure measurement processing shown in FIG. 10, is executed, and then executed is the processing of recording the arterial volume signals and the cuff pressures detected in steps S112 and S114 on the recording medium 132 in chronological order.

Figure 11:
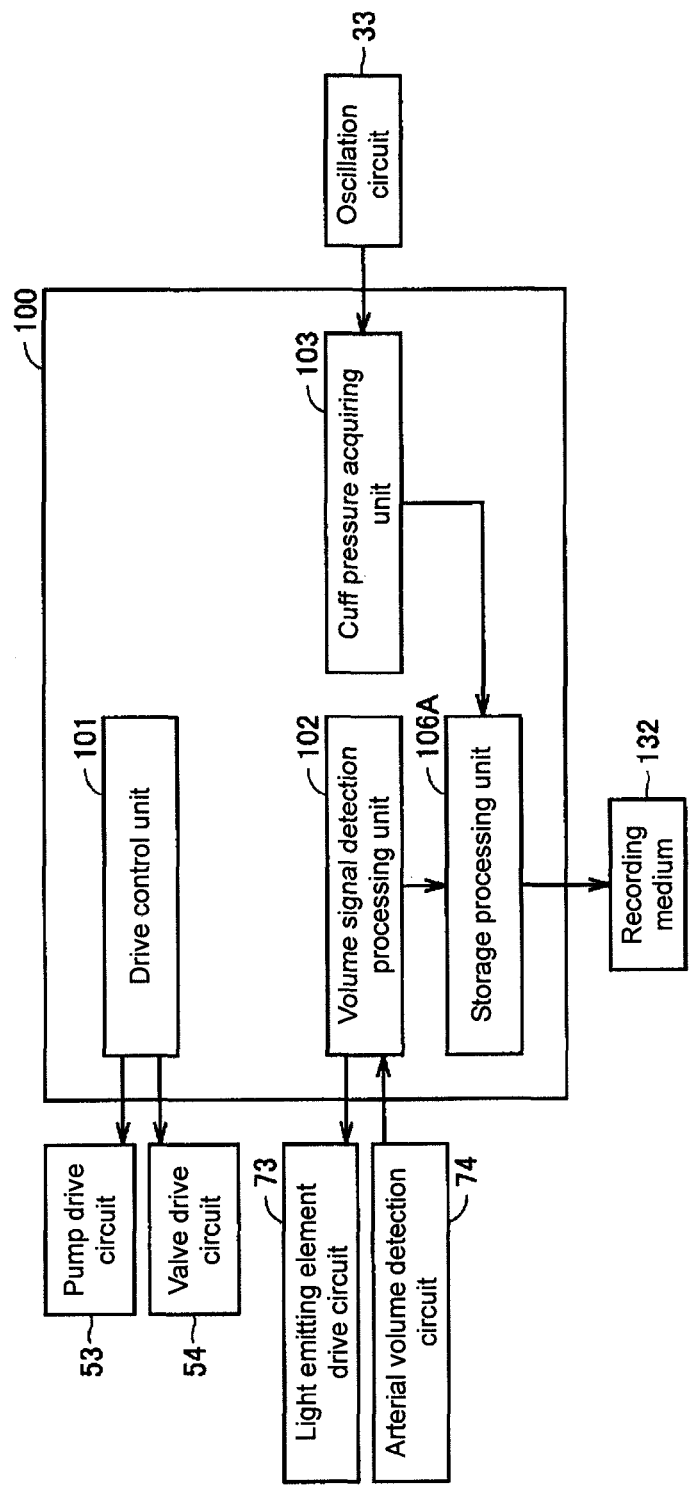
FIG. 11 is a functional block diagram showing a functional configuration of a sphygmomanometer in Modification 3 of the embodiment of the present invention.

FIG. 11 is a functional block diagram showing a functional configuration of the sphygmomanometer 1 in Modification 3 of the embodiment of the present invention.

Referring to FIG. 11, the CPU 100 of the sphygmomanometer 1 includes the drive control unit 101, the volume signal detection processing unit 102, the cuff pressure acquiring unit 103, and a storage processing unit 106A.

The storage processing unit 106A records, on the detachable recording medium 132, the measurement data including the arterial volume (volume pulse wave) data acquired by the volume signal detection processing unit 102, and the cuff pressure data acquired by the cuff pressure acquiring unit 103.

Figure 12:
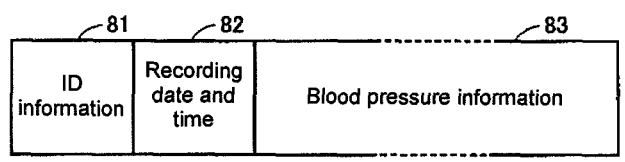
FIG. 12(a) is a diagram showing one example of a data structure of measurement data recorded on a recording medium in Modification 3 of the embodiment of the present invention.
FIG. 12(b) is a diagram showing a data structure of a blood pressure information field included in the measurement data.

FIG. 12(a) is a diagram showing one example of a data structure of measurement data 80 recorded on the recording medium 132 in Modification 3 of the embodiment of the present invention.

Referring to FIG. 12(a), each piece of the measurement data 80 stored in the recording medium 132 includes three fields 81 to 83 of "ID information", "recording date and time", and "blood pressure information" as one example. In outlines of contents of the respective fields, the "ID information" field 81 stores an identification number for specifying each piece of the measurement data, and the like, and the "recording date and time" field 82 stores the information such as the measurement date and time, and the measurement period of each piece of the measurement data, which are measured by the timing unit 45, and the like. Moreover, the "blood pressure information" field 83 stores the arterial volume data and the cuff pressure data for use in the derivation of the blood pressure.

FIG. 12(b) is a diagram showing a data structure of the blood pressure information field 83 included in the measurement data.

Referring to FIG. 12(b), the blood pressure information field 83 has an area 831 in which "time data" is stored, an area 832 in which the "arterial volume data" is stored, and an area 833 in which the "cuff pressure data" is stored.

In the area 831, a plurality of pieces of time data 1, 2, 3, . . . , N in accordance with a sampling cycle are stored. In the area 832, volume data V(1), V(2), . . . , V(n) is stored in association with the time data in the area 831, respectively. In the area 833, cuff pressure data P(1), P(2), . . . , P(n) is stored in association with the time data in the area 831, respectively.

The storage form is not limited to the above-described example, but the times (clock times) and the respective measurement values only need to be stored in association with one another.

Figure 13:
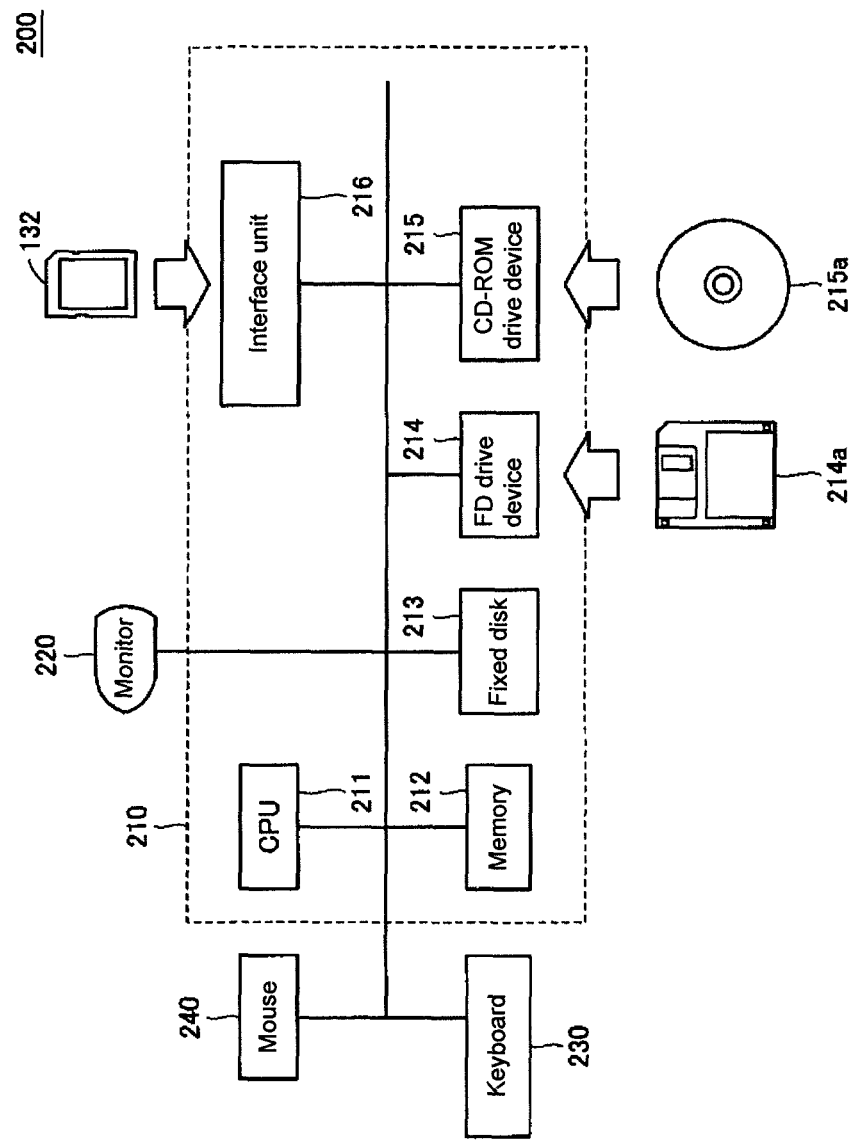
FIG. 13 is a block diagram showing one example of a hardware configuration of an information processing apparatus capable of executing the blood pressure derivation processing in Modification 3 of the embodiment of the present invention.

FIG. 13 is a block diagram showing one example of a hardware configuration of an information processing apparatus 200 that can execute the blood pressure derivation processing in Modification 3 of the embodiment of the present invention.

Referring to FIG. 13, the information processing apparatus 200 includes an information processing apparatus body 210, a monitor 220, a keyboard 230, and a mouse 240. The information processing apparatus body 210 includes a CPU 211, a memory 212, a fixed disk 213, which functions as a storage device, an FD (Flexible Disk) drive device 214, a CD-ROM (Compact Disk-Read Only Memory) drive device 215, and an interface unit 216. These types of hardware are connected to one another by a bus.

An FD 214a is loaded on the FD drive device 214, and a CD-ROM 215a is loaded on the CD-ROM drive device 215. The information processing apparatus 200 according to the present embodiment is realized by the CPU (Central Processing Unit) 211 executing software using the hardware such as the memory 212. Generally, such software is stored in a recording medium such as the FD 214a or the CD-ROM 215a, or is distributed through a network. Such software is read from the recording medium by the FD drive device 214, the CD-ROM drive device 215 or the like, or is received in a communication interface (not shown) to be stored on the fixed disk 213. Furthermore, it is read from the fixed disk 213 onto the memory 212, and is executed by the CPU 211.

The monitor 220 is a display unit to display the information such as the blood pressure outputted by the CPU 211, and as one example, is made of an LCD (Liquid Crystal Display), a CRT (Cathode Ray Tube), or the like. The mouse 240 receives an instruction from a user (representatively, a diagnosis performer such as a medical specialist) in accordance with the operation such as clicking and sliding. The keyboard 230 receives an instruction from the user in accordance with an inputted key. The CPU 211 is an arithmetic operation unit that conducts various arithmetic operations by sequentially executing programmed commands. The memory 212 stores various types of information in accordance with the program execution by the CPU 211. The interface unit 216 is a site to receive the measurement data 80 by the sphygmomanometer 1, and in the present embodiment, is formed by a slot through which the recording medium 132 can be loaded, a peripheral circuit that controls the slot, and the like. In place of the slot through which the recording medium 132 can be loaded, the interface unit may be configured as a communication interface unit capable of data communication with the sphygmomanometer 1. The fixed disk 213 is a nonvolatile storage device that stores programs executed by the CPU 211, and the arterial volume data as well as the cuff pressure data (measurement data 80) received from the sphygmomanometer 1. Moreover, to the information processing apparatus 200 may be connected an additional output apparatus such as a printer as needed.

The CPU 211 performs control to derive the blood pressure, based on the measurement data 80 stored in the fixed disk 213.

Figure 14:
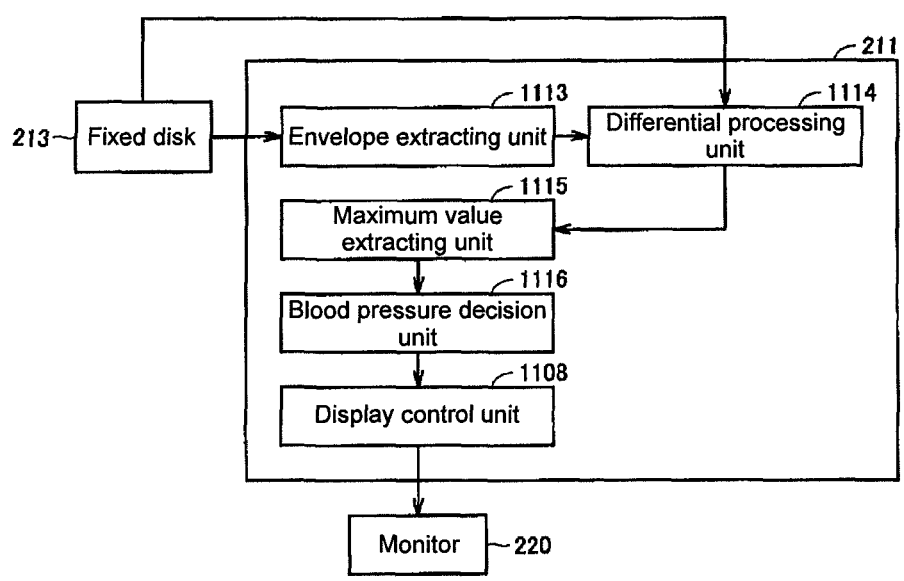
FIG. 14 is a functional block diagram showing a functional configuration of the information processing apparatus in Modification 3 of the embodiment of the present invention.

FIG. 14 is a functional block diagram showing functions of the information processing apparatus 200 in Modification 3 of the embodiment of the present invention.

Referring to FIG. 14, the CPU 211 of the information processing apparatus 200 includes an envelope extracting unit 1113, a differential processing unit 1114, a maximum value extracting unit 1115, a blood pressure decision unit 1116, and a display control unit 1108. The processing of these functional blocks is similar to the processing of the functional blocks shown in FIG. 3 (the envelope extracting unit 113, the differential processing unit 114, the maximum value extracting unit 115, the blood pressure decision unit 116, and the display control unit 108). Accordingly, descriptions thereof are not repeated here. The envelope extracting unit 1113 reads the measurement data 80 from the fixed disk 213 to extract the envelopes of the volume pulse wave (the volume minimum point envelope and the volume maximum point envelope). Moreover, the display control unit 1108 displays the systolic blood pressure and the diastolic blood pressure on the monitor 220.

The program to realize the blood pressure derivation processing in the above-described general information processing apparatus 200 (blood pressure derivation program) includes processing in steps S504, S506, S508, S510 and S126 of the blood pressure measurement processing shown in FIG. 10.

The blood pressure derivation program according to the present invention may call out necessary modules in a predetermined array at predetermined timing from among the program modules provided as a portion of an operating system (OS) of the computer so as to cause the necessary modules to execute the processing. In this case, the above-described modules are not included in the program itself, and the processing is executed in cooperation with the OS. The above-described program not including the modules may also be included in the program according to the present invention.

Moreover, the blood pressure derivation program according to the present invention may be provided by being incorporated in a portion of a different program. In this case as well, the program itself does not include the modules included in the above-mentioned different program, and the processing is executed in cooperation with the different program. The above-described program incorporated in the different program may be included in the program according to the present invention.

The blood pressure measurement method itself executed by the sphygmomanometer 1 in the embodiment or Modifications 1, 2 of the present invention can be provided as a program.

It should be considered that the embodiment disclosed this time is illustrative in all points and not limitative. The range of the present invention is indicated not by the foregoing descriptions but by the claims, and it is intended that meanings equivalent to the claims and all modifications within the range are included.

The invention claimed is:

1. A blood pressure measurement apparatus, comprising:
a cuff to be wound around a predetermined physical site of a measured person;
a pressure detector to detect a cuff pressure representing a pressure inside the cuff;
a volume detector to detect an arterial volume signal indicating a volume of an artery of the measured person;
an adjustment unit to adjust the pressure inside the cuff;
a drive control unit to control driving of the adjustment unit; and
a derivation control unit to perform derivation control to derive a blood pressure of the measured person, based on the cuff pressure and the arterial volume signal, the derivation control unit including:
a first extraction unit to extract an envelope of a volume pulse wave based on the arterial volume signal;
a differential unit to differentiate the envelope with respect to the cuff pressure;
a second extraction unit to extract a maximum value of a differential value of the envelope' and
a decision unit to measure the blood pressure based on the cuff pressure obtained when the maximum value of the differential value is extracted,
wherein the envelope includes a volume minimum point envelope in contact with arterial volume minimum points of respective pulse wave components included in the volume pulse wave, and a volume maximum point envelope in contact with arterial volume maximum points of the respective pulse wave components included in the volume pulse wave,
wherein the differential unit differentiates the volume minimum point envelope, and the volume maximum point envelope,
wherein the second extraction unit extracts a maximum value of a differential value of the volume minimum point envelope, and a maximum value of a differential value of the volume maximum point envelope,
wherein the derivation control unit performs the derivation control when the cuff pressure is being decreased or increased at a constant rate by the drive control unit, and
wherein the decision unit measures, as a diastolic blood pressure, the cuff pressure obtained when the maximum value of the differential value of the volume minimum point envelope is extracted by the second extraction unit, and as a systolic blood pressure, the cuff pressure obtained when the maximum value of a differential value of the volume maximum point envelope is extracted by the second extraction unit.

2. A blood pressure measurement apparatus, comprising:
a cuff to be wound around a predetermined physical site of a measured person;
a pressure detector to detect a cuff pressure representing a pressure inside the cuff;
a volume detector to detect an arterial volume signal indicating a volume of an artery of the measured person;
an adjustment unit to adjust the pressure inside the cuff;
a drive control unit to control driving of the adjustment unit; and
a derivation control unit to perform derivation control to derive a blood pressure of the measured person, based on the cuff pressure and the arterial volume signal, the derivation control unit including:
a first extraction unit to extract an envelope of a volume pulse wave based on the arterial volume signal;
a differential unit to differentiate the envelope with respect to the cuff pressure;
a second extraction unit to extract a maximum value of a different value of the envelope; and
a decision unit to measure the blood pressure based on the cuff pressure obtained when the maximum value of the differential value is extracted,
wherein the envelope includes a volume minimum point envelope in contact with arterial volume minimum points of respective pulse wave components included in the volume pulse wave, and a volume maximum point envelope in contact with arterial volume maximum points of the respective pulse wave components included in the volume pulse wave, wherein the differential unit differentiates the volume minimum point envelope, and the volume maximum point envelope, wherein the second extraction unit extracts a maximum value of a differential value of the volume minimum point envelope, and a maximum value of a differential value of the volume maximum point envelope, wherein the derivation control unit performs the derivation control when the cuff pressure is controlled so as to be decreased or increased in stages by a predetermined pressure difference by the drive control unit, wherein the decision unit measures, as a diastolic blood pressure, the cuff pressure obtained when the maximum value of the differential value of the volume minimum point envelope is extracted by the second extraction unit, and as a systolic blood pressure, the cuff pressure obtained when the maximum value of a differential value of the volume maximum point envelope is extracted by the second extraction unit, and wherein the decision unit measures the blood pressure by correcting the cuff pressure.

3. The blood pressure measurement apparatus according to claim 2, wherein the second extraction unit further extracts differential values before and after the maximum value, and wherein the decision unit measures the diastolic blood pressure by correcting the cuff pressure based on the maximum value, the differential values before and after the maximum value, and the predetermined pressure difference.

4. The blood pressure measurement apparatus according to claim 2, wherein the second extraction unit further extracts differential values before and after the maximum value, and wherein the decision unit measures the a systolic blood pressure by correcting the cuff pressure based on the maximum value, the differential values before and after the maximum value, and the predetermined pressure difference.

5. The blood pressure measurement apparatus according to claim 1, wherein the volume detector includes:

a light emitting element to emit light to the artery; and a light receiving element to receive light transmitted through or light reflected at the artery of the light emitted by the light emitting element.

6. The blood pressure measurement apparatus according to claim 1, wherein the volume detector includes a plurality of electrodes to detect impedance of a site including the artery.

7. The blood pressure measurement apparatus according to claim 2, wherein the volume detector includes:

a light emitting element to emit light to the artery; and a light receiving element to receive light transmitted through or light reflected at the artery of the light emitted by the light emitting element.

8. The blood pressure measurement apparatus according to claim 3, wherein the volume detector includes:

a light emitting element to emit light to the artery; and a light receiving element to receive light transmitted through or light reflected at the artery of the light emitted by the light emitting element.

9. The blood pressure measurement apparatus according to claim 4, wherein the volume detector includes:

a light emitting element to emit light to the artery; and a light receiving element to receive light transmitted through or light reflected at the artery of the light emitted by the light emitting element.

10. The blood pressure measurement apparatus according to claim 2, wherein the volume detector includes a plurality of electrodes to detect impedance of a site including the artery.

11. The blood pressure measurement apparatus according to claim 3, wherein the volume detector includes a plurality of electrodes to detect impedance of a site including the artery.

12. The blood pressure measurement apparatus according to claim 4, wherein the volume detector includes a plurality of electrodes to detect impedance of a site including the artery.

* * * * *